United States Patent
Rutner et al.

(10) Patent No.: US 6,254,570 B1
(45) Date of Patent: Jul. 3, 2001

(54) BACK-UP RETENTION MEMBER DRAINAGE CATHETER

(75) Inventors: Alvin B. Rutner, Los Altos, CA (US); Frederick D. Roemer, Bloomington, IN (US)

(73) Assignee: Vance Products, Inc., Spencer, IN (US)

( * ) Notice: Subject to any disclaimer, the term of this patent is extended or adjusted under 35 U.S.C. 154(b) by 0 days.

(21) Appl. No.: 09/056,437

(22) Filed: Apr. 7, 1998

Related U.S. Application Data

(60) Provisional application No. 60/043,484, filed on Apr. 7, 1997.

(51) Int. Cl.[7] .................................................. A61M 29/00
(52) U.S. Cl. ................. 604/101.02; 606/190; 604/96.01; 604/101.01; 604/509
(58) Field of Search ............................ 604/96, 101, 174, 604/96.01, 101.01, 101.02, 101.03, 102.01, 102.02, 102.03, 103.07, 264, 43, 508, 509, 93.01, 99.01, 167.01, 238, 274, 921; 606/191–197

(56) References Cited

U.S. PATENT DOCUMENTS

| | | |
|---|---|---|
| 3,211,152 | 10/1965 | Stern . |
| 3,659,612 | 5/1972 | Shiley et al. . |
| 4,335,723 * | 6/1982 | Patel ...................................... 128/349 |
| 4,338,942 | 7/1982 | Fogarty ................................. 128/344 |
| 4,369,789 | 1/1983 | LeVeen et al. .......................... 604/96 |
| 4,403,612 | 9/1983 | Fogarty ................................. 128/344 |
| 4,885,003 | 12/1989 | Hillstead ................................ 604/22 |
| 4,932,956 | 6/1990 | Reddy et al. . |
| 4,994,033 | 2/1991 | Shockey et al. ...................... 604/101 |
| 5,038,777 | 8/1991 | Dunn . |
| 5,226,889 | 7/1993 | Sheiban . |
| 5,358,487 | 10/1994 | Miller ..................................... 604/96 |
| 5,366,472 | 11/1994 | Hillstead .............................. 606/194 |
| 5,470,350 * | 11/1995 | Buchholtz et al. ..................... 607/97 |
| 5,520,646 * | 5/1996 | D'Andrea ................................ 604/96 |
| 5,536,252 | 7/1996 | Imran et al. ........................... 604/101 |
| 5,707,358 * | 1/1998 | Wright ................................... 604/96 |

FOREIGN PATENT DOCUMENTS

| | | | |
|---|---|---|---|
| 0266957 | 5/1988 | (EP) . | |
| 0 266 957 * | 5/1988 | (EP) ............................... 604/101.02 |
| 9638192 | 12/1996 | (WO) . | |

* cited by examiner

Primary Examiner—Richard K. Seidel
Assistant Examiner—Jennifer Maynard
(74) Attorney, Agent, or Firm—Richard J. Godlewski; Anton P. Ness; James B. Hunt

(57) ABSTRACT

A back-up retention member drainage catheter (10) for insertion in the bladder and urethra of a patient undergoing a radical prostatectomy surgical procedure. The drainage catheter includes an elongated tubular member (11) having a drainage lumen (14) extending longitudinally therein with an external drainage port (15, 16) disposed near the distal end (12) of the tubular member. A back-up retention member (18) and, in particular, a first balloon (20) is disposed on the elongated tubular member near the distal end and proximal the external drainage port. A primary retention member (19) and, in particular, a second retention balloon (22) is also disposed on the elongated tubular member around the first retention balloon. First and second inflation lumens (21, 23) extend longitudinally through the elongated tubular member and communicate internally with the first and second retention balloons, respectively. To maintain independent inflation of the two retention balloons, the second inflation lumen communicates externally with the first retention balloon. To maintain the balloons in an expanded state, first and second one-way valves (27, 29) are disposed at the proximal end of the first and second inflation lumens, respectively. A suture tether (31) is positioned through a tether lumen (26) for securing the drainage catheter percutaneously through the patient should the physician so desire.

17 Claims, 7 Drawing Sheets

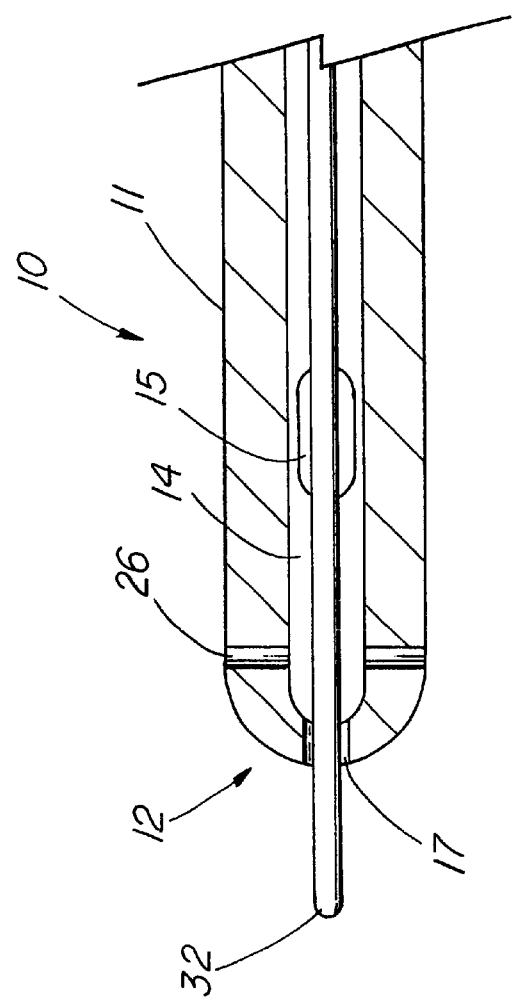
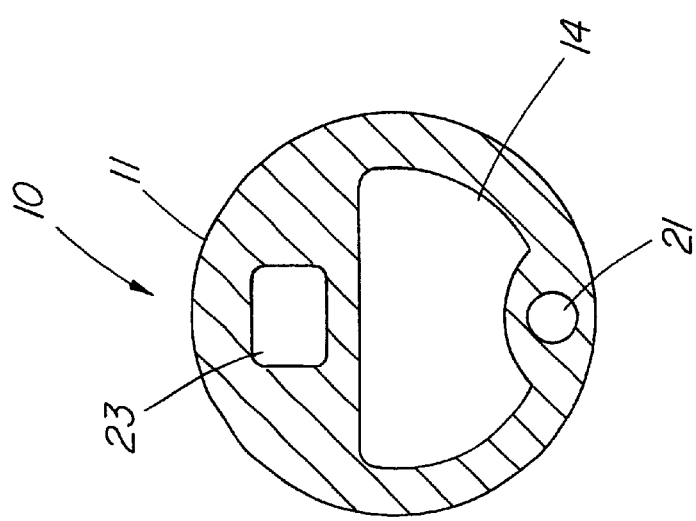

BACK-UP RETENTION MEMBER DRAINAGE CATHETER

CROSS-REFERENCE TO RELATED APPLICATIONS

This application claims priority of provisional application Serial No. 60/043,484, filed Apr. 7, 1997.

TECHNICAL FIELD

The invention relates generally to medical devices and, in particular, to a drainage catheter with a back-up retention member for retaining the catheter in a patient.

BACKGROUND OF THE INVENTION

Since the 1930's, the Foley drainage catheter has remained the preferred option for patients requiring urinary diversion. The basic design of one or more drainage ports at or near the distal end, a central drainage lumen, an elastomeric retention balloon for anchoring the catheter in the bladder, and a proximally-located valve to keep the fluid from leaking out the inflation lumen and deflating the balloon, has not undergone significant evolution other than the change from latex to silicone.

The Foley catheter does have some acknowledged weaknesses. Chief among them is displacement of the catheter due to accidental or intentional dislodgement from the bladder, which may be attributed to the patient pulling on the proximal exposed portion. There is much greater risk of dislodgement if the balloon has partially or fully deflated due to a leak at the proximal valve or balloon itself, or due to the natural diffusion of the balloon contents over time through a semi-permeable balloon material.

While dislodgement of a Foley catheter is not usually serious in most instances, it can be a very large problem in patients who have undergone a radical prostatectomy where the prostate has been removed and the urethra resectioned. The standard procedure for prostatectomy patients is to place a Foley drainage catheter at the time of surgery to be left in place for no more than two to three weeks. Besides providing drainage, the catheter keeps the anastomotic site patent during the healing process and offers some degree of protection from strain and trauma. If the catheter is dislodged, however, it can damage the delicate anastomotic site, especially early in the post-surgical recovery period. Even if the sutures at the site do not pull out during dislodgement, the surgeon may be forced to reopen the patient to place another drainage catheter to prevent possible damage during its introduction through the surgical resection site.

Given the seriousness of having a Foley drainage catheter dislodge following a surgical procedure such as a radical prostatectomy, there is a strong need for a catheter design that helps preclude the balloon or retention member from displacing and causing damage to the surgical site. Existing devices do not provide this important safety feature of retaining the catheter inside the bladder.

In addition to the Foley catheter for urinary drainage, there are catheters used in gastric, vascular, and other procedures that utilize a balloon or other means for retention, occlusion or dilatation in which deflation or a related failure could be critical.

SUMMARY OF THE INVENTION

The foregoing problems are solved and a technical advance is achieved in an illustrative back-up retention member drainage catheter for placement in the bladder of a patient. This drainage catheter is particularly advantageous during and after a radical prostatectomy surgical procedure for insuring that the catheter is retained in the bladder of a patient during the healing process of the resectioned urethra. The drainage catheter of the present invention includes an elongated tubular member having a drainage lumen extending longitudinally therein with at least one external drainage port disposed at least near the distal end thereof. A back-up retention member having an expanded state is disposed on the elongated member at least near the distal end and proximal the external drainage port. A primary retention member having an expanded state is also disposed on the elongated member and about the back-up retention member. As a result, the back-up retention member advantageously maintains the position of the drainage catheter in the bladder of a patient should the primary retention member fail in the expanded state and collapse. The back-up retention member is particularly advantageous during and after a radical prostatectomy surgical procedure to eliminate the need for another surgical procedure to reinsert another drainage catheter in the bladder through the resectioned urethra. Maintaining the drainage catheter through the resectioned urethra is absolutely necessary to maintain the patency of the urethra during the healing process.

In the preferred embodiment, the back-up and primary retention members comprise first and second balloons each having a collapsed and an expanded state. To independently inflate the balloons to the expanded state, the elongated member further includes first and second inflation lumens extending longitudinally therein and communicating internally and independently with the first and second balloons, respectively. In addition, the second inflation lumen communicates externally with the first balloon so as to maintain independent inflation. First and second one-way valves are disposed near the proximal end of the first and second inflations lumen, respectively.

The distal end of the elongated member includes a plug having an atraumatic shape that closes the drainage and inflation lumens thereat. The elongated member, as well as the back-up and primary retention balloons, comprise a soft and flexible material such as silicone. However, the soft and flexible material can comprise at least one from a group consisting of silicone, latex, or any other elastomeric material.

To further advantageously retain the drainage catheter in the bladder of a patient, the elongated member includes a tether lumen extending transversely therethrough and disposed at least near the distal end and distal to the external drainage port. The catheter also includes a tether which is positionable through the tether lumen for percutaneous securement to the patient via the bladder.

In another aspect of the drainage catheter, another external drainage port is disposed at the distal end of the elongated member. This distal end drainage port advantageously permits a wire guide to be extended distally from the drainage lumen and the external drainage port. The wire guide is used to position the drainage catheter in the patient. Furthermore, the external drainage port at the distal end of the catheter advantageously permits endoscopic instruments and other medical devices to be inserted therethrough and in, for example, the ureters of the patient.

To maintain the retention balloons in the expanded state, one way valves are positioned at the proximal end of the inflation lumens to advantageously maintain saline in the expanded balloons and inflation lumens.

In addition to acting as retention arrangements the balloons also act as seals for preventing the flow of fluid from the bladder into the urethra around the outer surface of elongated tube member. Such a flow of fluid would prevent the healing process following a prostatectomy. Collapse of the outer balloon would result in the inner balloon taking over the same function. The inner balloon is fixed to the member in an offset manner with the two balloons in contact with one another at the proximal contact points and spaced from one another at the distal contact or fixing points to member. The offsetting of the balloons in this way unexpectedly maintains the seal between the bladder and the urethra at all times.

BRIEF DESCRIPTION OF THE DRAWING

FIG. 4 depicts an enlarged cross-sectional view of the elongated tubular member of the drainage catheter of FIG. 2 taken along line 4—4;

FIG. 5 depicts an enlarged longitudinally sectioned view of the distal portion of another embodiment of the drainage catheter of FIG. 1;

DETAILED DESCRIPTION

Figure 1:
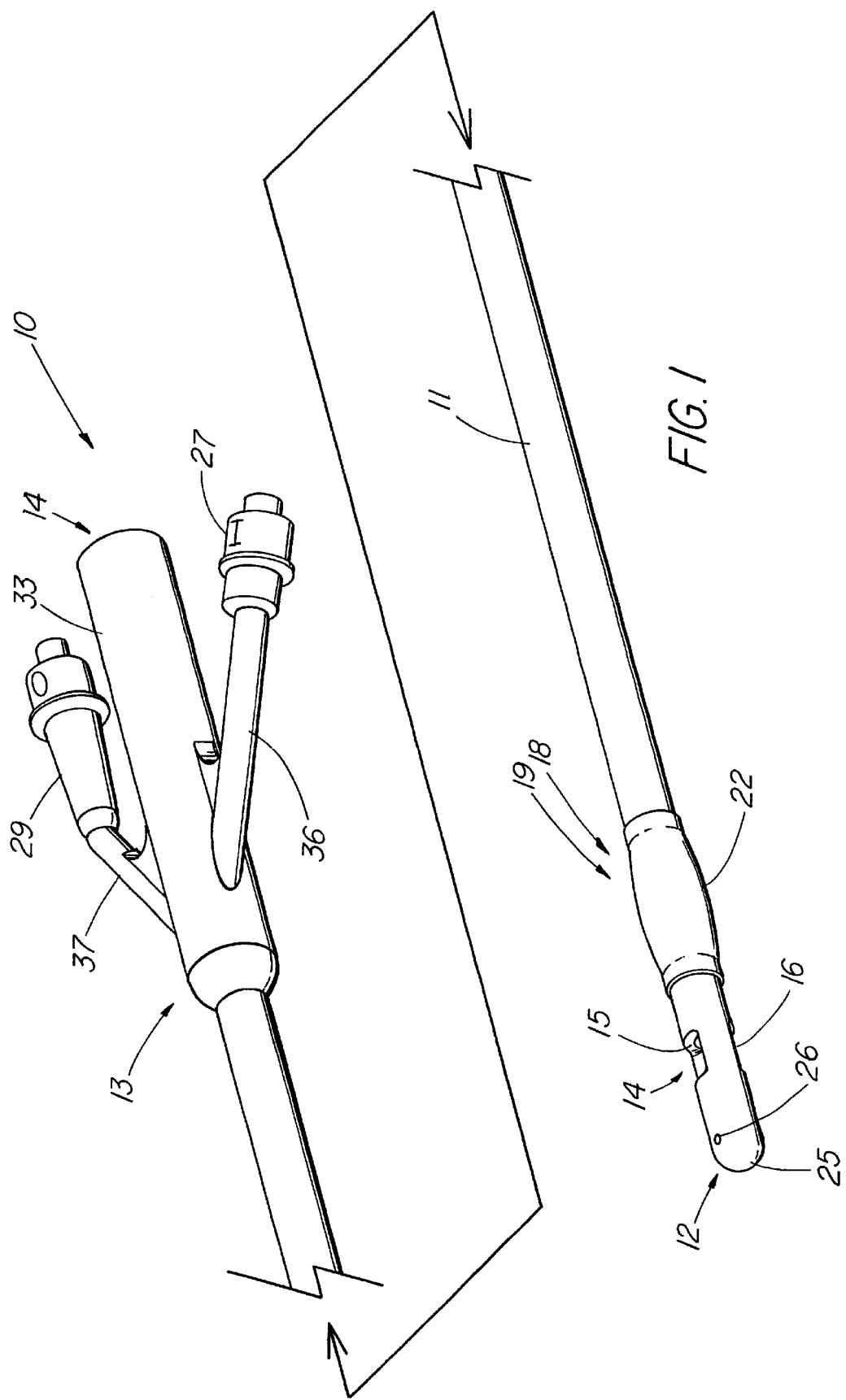
FIG. 1 depicts a pictorial view of a back-up retention member drainage catheter of the present invention.

FIG. 1 depicts a pictorial view of a preferred illustrative embodiment of back-up retention member drainage catheter 10 that is insertable into the bladder of a patient through the urethra. The drainage catheter includes an elongated tubular member 11 having a distal end 12, a proximal end 13 and a drainage lumen 14 that extends longitudinally therein. At least one external drainage port 15 and, preferably, a pair of diametrically opposed side drainage ports 15 and 16 are disposed at least near the distal end of the elongated tubular member. Distal end 12 of the elongated tubular member along with drainage ports 15 and 16 are positioned in the bladder of a patient for urine to flow into drainage lumen 14 via the drainage ports. Urine flows through the drainage lumen and out proximal end 13 of the catheter via connector hub 33, which is typically connected to a urine collection bag (not shown). To minimize trauma to the patient during insertion of the catheter into the bladder, distal end 12 of the elongated tubular member has an atraumatic shape 25, which is preferably hemispherical.

To retain the drainage catheter in the bladder of the patient, catheter 10 includes an outer, primary retention member 19 and an inner, back-up retention member 18 that are disposed on the outer surface of the elongated member at least near distal end 12 of the catheter and proximal the external drainage ports 15 and 16. In this preferred embodiment, primary retention member 19 comprises a second balloon 22 disposed around back-up retention member 18.

Figure 2:
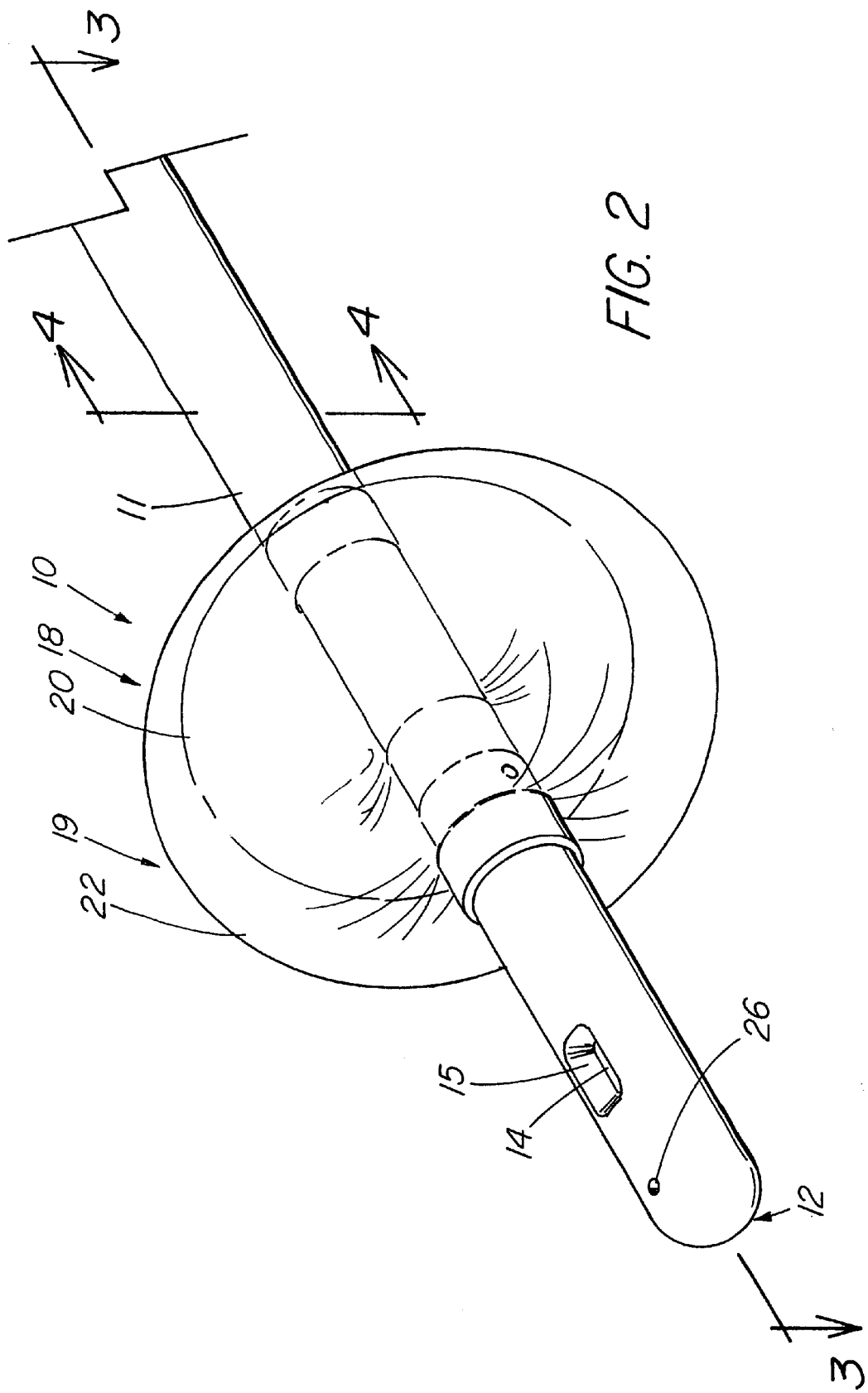
FIG. 2 depicts an enlarged pictorial view of the distal portion of the drainage catheter of FIG. 1 with the outer, primary retention member and the inner, back-up retention member in an expanded state.

FIG. 2 depicts an enlarged pictorial view of the distal portion of elongated tubular member 11 of drainage catheter 10 of FIG. 1 with outer, primary retention member 19 and inner, back-up retention member 18 in an expanded state. As previously suggested, outer, primary retention member 19 preferably comprises a second balloon 22 of a silicone material. The second balloon is disposed around inner, back-up retention member 18, which is preferably a first balloon 20 also of a silicone material. Elongated tubular member 14 is also preferably of a silicone material, but can be any soft and flexible material such as latex rubber or any other elastomeric material. Being of the same soft and flexible material, back-up and primary balloons 20 and 22 can be readily attached in an independent manner to the outer surface of the elongated member using, for example, a commercially available, medical-grade silicone adhesive. This independent attachment allows either of the balloons to remain individually in an expanded state without the inflation or assistance of the other balloon. This independent attachment and expansion also advantageously permits either balloon to remain in an expanded state should the other fail. With most Foley drainage catheters, the balloon material can have a manufacturing defect or weakness therein. Additionally, the attending physician can breach the integrity of the balloon material, or the one-way valve at the other end of the inflation lumen for the balloon can be weak or experience a failure. As a result, a single retention balloon deflates into a collapsed state allowing the unintentional or inadvertent removal of the drainage catheter from the bladder of the patient.

Expanded retention balloons 20 and 22 are positioned on the outer surface of the elongated tubular member proximal to external drainage port 15. However, the distal portion of elongated tubular member 11 extending distally from the two retention balloons should be as short as possible to optimize drainage from the bladder of the patient. In addition to drainage lumen 14 extending longitudinally therethrough, elongated tubular member 11 includes a tether lumen 26 that extends transversely through the member and is disposed near distal end 12 distal to external drainage port 15. A suture or tether may be inserted through the tether lumen, passed through the bladder neck, anterior bladder wall, and then through the abdominal wall to be anchored to the skin. After the distal portion of the elongated member is positioned in the bladder of a patient undergoing a radical prostatectomy, it is imperative that the drainage catheter remain in the resectioned urethra to maintain the patency thereof. As a result, first and second retention balloons 20 and 22 are utilized as a back-up for each other should either of these balloons deflate. As a result, the need for a second surgical procedure to reinsert another drainage balloon is minimized, if not totally eliminated.

Figure 3:
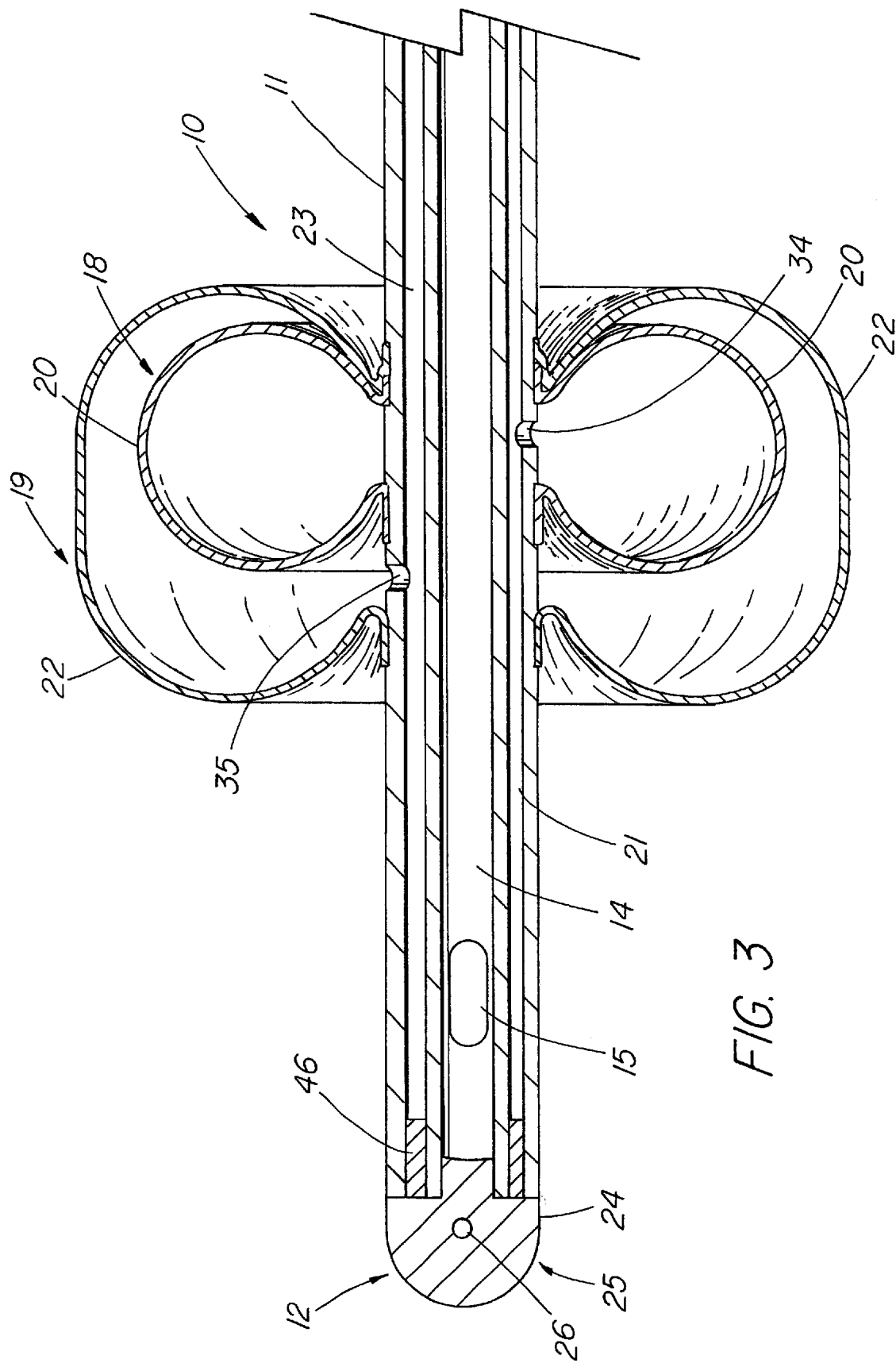
FIG. 3 is an enlarged, longitudinally sectioned view of the distal portion of the drainage catheter of FIG. 2 taken along the line 3—3.

FIG. 3 is an enlarged, longitudinally sectioned view of the distal portion of elongated tubular member 11 of drainage catheter 10 of FIG. 2 taken along the line 3—3. Back-up and primary retentions members 18 and 19 and, in particular, first and second retention balloons 20 and 22 are shown in an expanded state and attached to the outer surface of elongated tubular member 11 just proximal side drainage port 15. The first and second balloons are independently attached to the outer surface for independent inflation to the expanded state. Elongated tubular member 11 includes drainage lumen 14 extending longitudinally therein with external access via side drainage port 15. Also extending longitudinally in the walls of the elongated tubular member are first and second inflation lumens 21 and 23. First inflation lumen 21 communicates with the interior of back-up retention balloon 20 via first inflation lumen port 34. The inflation lumen and port are used to supply saline typically to the interior of back-up retention balloon 20 for inflation to the expanded state. Similarly, second inflation lumen 23 communicates with the interior of primary retention balloon 22 via second inflation lumen port 35. To maintain independent access to each of the first and second balloons, second inflation lumen access port 35 is positioned externally to back-up retention balloon 20.

By way of example, elongated member 11 is a tubular member having an outside diameter ranging from 6 French to 28 French (2.0 mm to 9.3 mm; 0.092 inches to 0.367 inches). Preferably, this back-up retention member drainage catheter has an. outside diameter of 20 French (7.3 mm; 0.288 inches). The overall length of the drainage catheter can range from 12 to 24 inches; however, the preferred length is approximately 17 inches. First inflation lumen 21 has a diameter of approximately of 0.038 inches, whereas second inflation lumen 23 has a rectangular shape with a side dimension of approximately 0.055 inches. Drainage lumen 14 has a semi-circular cross-sectional shape with a diameter of approximately 0.185 inches.

FIG. 4 depicts an enlarged cross-sectional view of elongated tubular member 11 of drainage catheter 10 of FIG. 2 taken along line 4—4. This cross-sectional view further illustrates the position and size of first inflation lumen 21, second inflation lumen 23 and drainage lumen 14 as described with respect to FIG. 3.

Returning the reader's attention to FIG. 3, distal end 12 of elongated tubular member includes a plug 24 having an atraumatic shape 25 such as a hemispherical shape with tether lumen 26 extending transversely therethrough. Tether lumen 26 is approximately 1.5 mm in diameter and is disposed at least near distal end 12 and distal, external drainage port 15. Side port lumens 15 and 16 are elliptical in shape with a major diameter of approximately 6 mm and a minor diameter of approximately 3 mm. Hemispherical plug 24 has a segment extending proximally therefrom and into drainage lumen 14. A medical-grade silicone plug 46 is inserted into first and second inflation lumens 21 and 23 and applied to plug 24 to close the distal end of elongated tubular member 11. Elongated tubular member 11 is formed from a soft and flexible material and, in particular, silicone. The elongated tubular member, as well as the first and second retention balloons are preferably formed of the same silicone material; however, the soft and flexible material can also be from a group consisting of silicone, latex rubber, or any other elastomeric material. First and second retention balloons 20 and 22 are formed preferably of a silicone material and can range in size from 0 to 30 cc in volume when in their expanded state. Preferably, each of the first and second balloons are inflated with 15 cc of fluid . As primary retention balloon 22 would have a total volume of 30 cc of saline including, of course, the 15 cc volume of back-up retention balloon 20. Should primary retention balloon 22 collapse due to a defect in the balloon wall material, physician mishandling, or any other reason, back-up retention balloon 20 would still be in the expanded state and still retain the drainage catheter in the bladder of the patient.

Returning the reader's attention to FIG. 1, one-way valves 27 and 29 are connected to first and second side arms 36 and 37, respectively, which extend first and second inflation lumens 21 and 23 from drainage connector hub 33. These one-way valves are commercially available and commonly known as Halwkey Roberts one-way valves. These valves are used to inflate the first and second retention balloons to an expanded state with saline. The valves close so as to prevent escape of saline and to keep the retention balloons in their expanded state.

FIG. 5 depicts an enlarged longitudinally sectioned view of the distal portion of another embodiment of drainage catheter 10 of FIG. 1. In this embodiment, distal end 12 of the elongated tubular member 11 has a drainage or access port 17, which is in-line with drainage lumen 14. This particular configuration with an access or drainage port at the very distal end of the catheter is commonly known as a Councill-Foley catheter. This particular configuration of a Foley catheter permits the drainage catheter to be inserted over a wireguide 32, which is used in various surgical procedures. In addition, endoscopic instruments and other medical devices can likewise be inserted through the Foley catheter for access, for example, to the ureters via the urethra and bladder. In this particular embodiment, side drainage ports 15 and 16 are also included for access to the drainage lumen. In addition, tether lumen 26 extends transversely across the elongated member near distal end 12.

Figure 6:
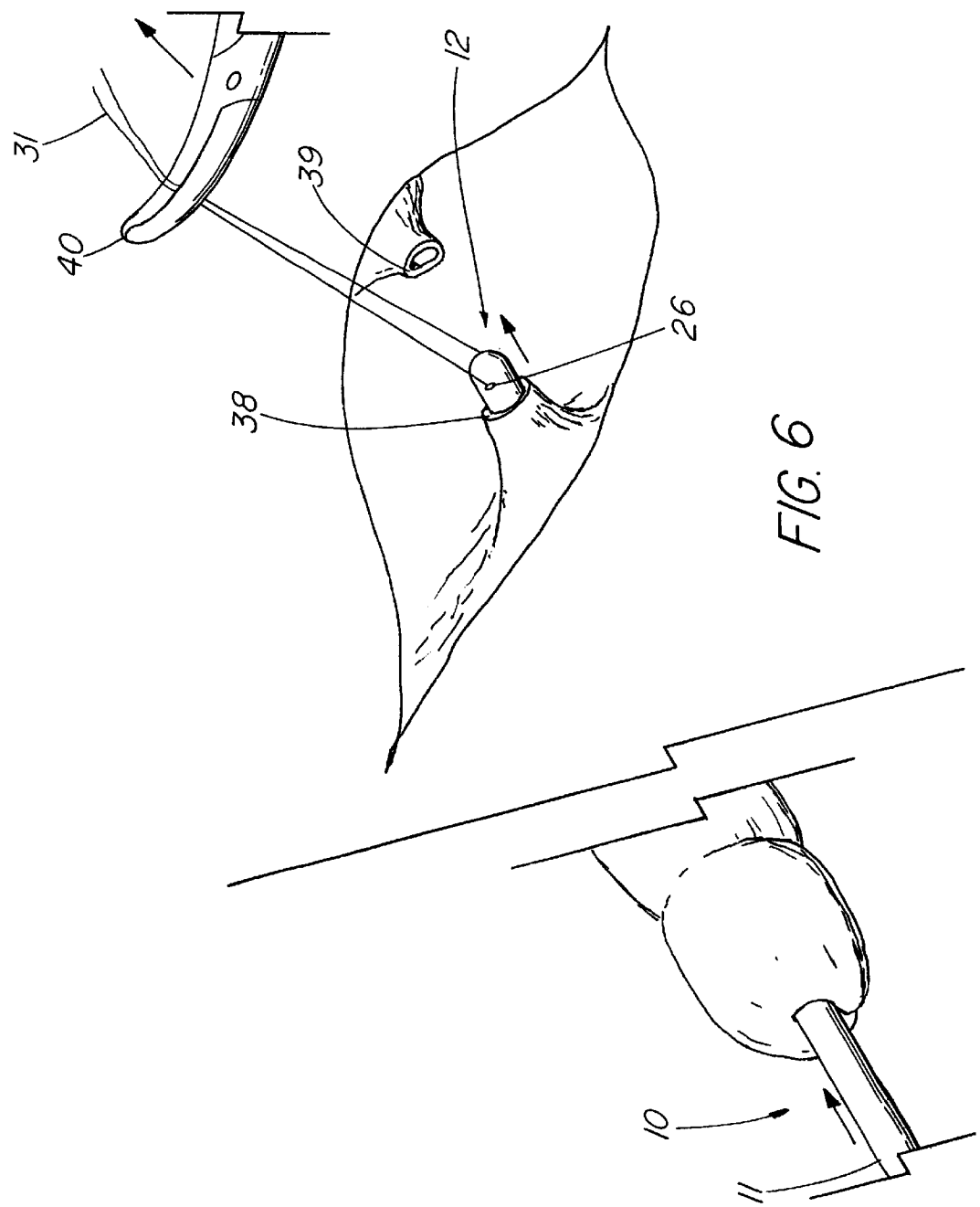
FIG. 6 depicts placement of the drainage catheter of the present invention through the urethra of a patient undergoing a radical prostatectomy surgical procedure.

FIG. 6 depicts placement of drainage catheter 10 of the present invention emerging via urethral stump 38 of a patient undergoing a radical prostatectomy. Distal end 12 of elongated tubular member 11 is inserted through the penile shaft toward bladder neck 39 after the prostate of the patient has been surgically removed. Suture tether 31 may be positioned through tether lumen 26 of the catheter. Forceps 40 can be used with the suture tether to adjust the position of the catheter after it is passed through the urethra and emerges through the urethral stump.

Figure 7:
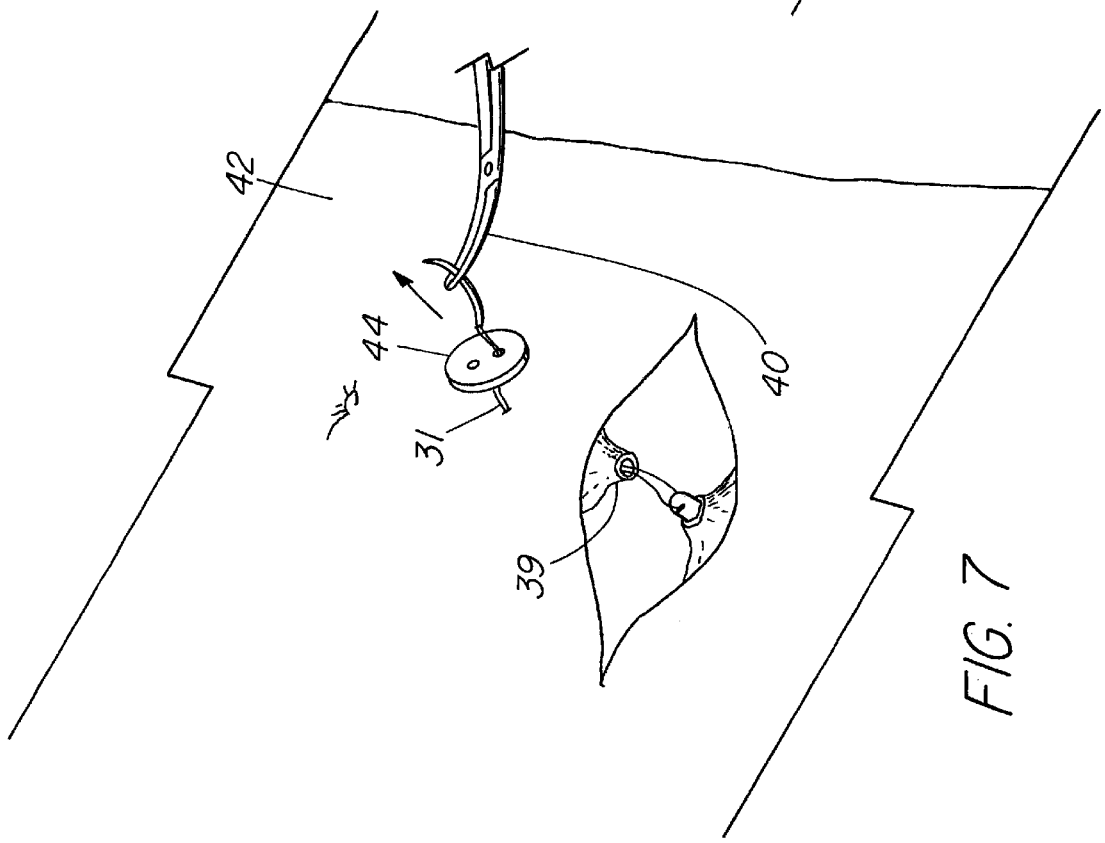
FIG. 7 depicts a tether of the drainage catheter being inserted through the bladder neck and percutaneously through the patient's skin.

FIG. 7 depicts suture tether 31 being inserted through bladder neck 39, through the anterior bladder wall and abdominal wall and then percutaneously through the patient's skin 42 lateral to the midline. The suture tether suture is placed through a retention disk 44 for fastening the suture tether externally to the patient.

Figure 8:
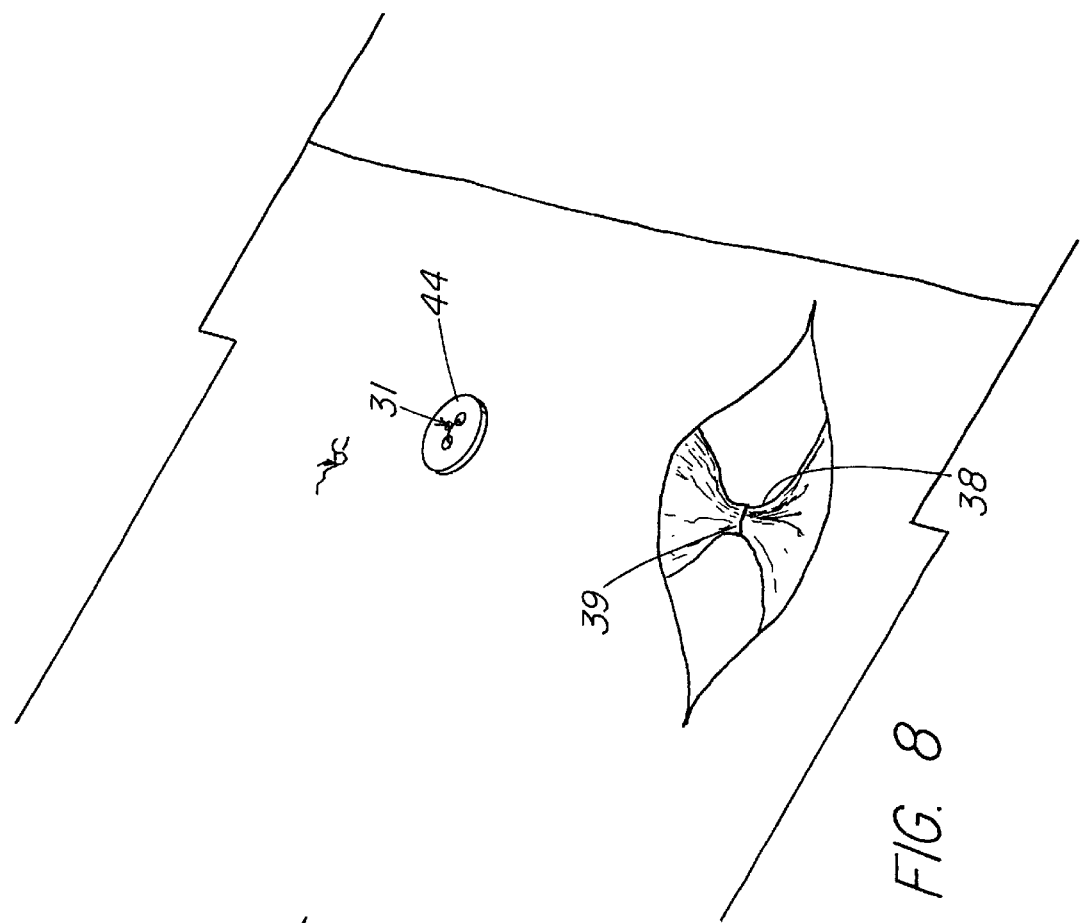
FIG. 8 depicts the bladder neck and the penile urethra of a patient being resectioned during the radical prostatectomy procedure.

FIG. 8 depicts bladder neck 39 and the penile urethra 38 following anastomosis during the radical prostatectomy procedure with the drainage balloon positioned in the bladder. Suture tether 31 is then affixed to retention disk 44 for securely fastening the drainage catheter in the bladder of a patient. Although this surgical procedure has been depicted utilizing a suture tether for additional anchorage of the drainage catheter in the bladder of a patient, this is not a requirement for the procedure. The suture tether is also not required for the back-up retention member catheter to be fully operational in the bladder of the patient. Securing the suture tether percutaneously to the patient is an optional feature when desired by the attending physician.

Figure 9:
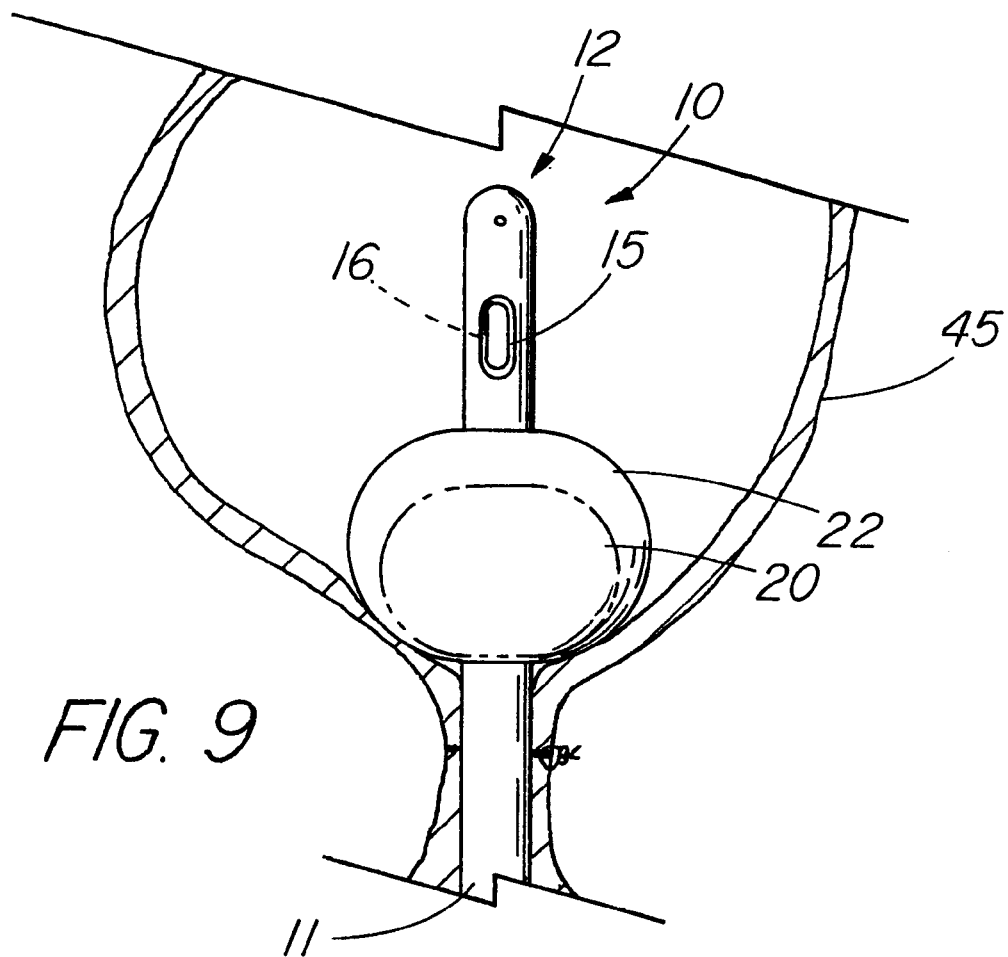
FIG. 9 depicts the drainage catheter of the present invention positioned in the bladder of a patient.

FIG. 9 depicts drainage catheter 10, and in particular, distal end 12 thereof with back-up and primary retention balloons 20 and 22 in an expanded state in bladder 45 of a patient. The retention balloons are positioned adjacent the bladder neck so as to minimize the drainage of urine through the resectioned urethra. Urine enters external drainage ports 15 and 16 for drainage into a collection bag via the drainage lumen of the catheter. Should primary retention balloon 22 fail for whatever reason, back-up retention balloon 20 will retain the distal end of the drainage catheter in the bladder.

It is to be understood that the above-described back-up retention member drainage catheter is merely an illustrative embodiment of the principles of this invention and that other back-up retention member drainage catheters can be devised by those skilled in the art without departing from the spirit and scope of this invention. For example, the primary and back-up retention members have been described as balloons. Alternatively, the back-up retention member can be any mechanically expandable arrangement such as a plurality of slits formed in the outer surface of the drainage catheter allowing the slits to mechanically expand during longitudinal compression of the catheter. This arrangement is commonly referred to as a Malecot retention mechanism. This mechanical expansion mechanism could be fully contained within the primary inflation balloon. Likewise, the primary retention member could also be a mechanical expansion mechanism that is similar to or different in construction from that of the back-up retention member. Selection of materials for the drainage catheter is based on minimizing trauma or irritation to the patient. Latex rubber and silicone have been typically used in the past as the soft and flexible material. However, any other elastomeric material with for example reinforcing braid or mesh can be similarly utilized. This back-up retention member drainage balloon can be useful for safe retention in the kidney. It can also be useful in all other specialities such as tubes in the stomach or bowel for feeding or decompression of the bowel, abdominal or chest cysts, abcesses, etc. It can also be useful for drainage of the gallbladder.

What is claimed is:

1. A back-up retention member drainage catheter comprising:
    an elongated member having a distal end, a proximal end and a drainage lumen extending longitudinally therein and having at least one external drainage port disposed at least near said distal end; wherein said distal end of said elongated member includes a plug insertable into said drainage lumen and at least one inflation lumen, said plug having an atraumatic shape and closing said drainage lumen and at least one inflation lumen thereat;
    a back-up retention member having an expanded state and disposed on said elongated member at least near said distal end and proximal said at least one external drainage port; and
    a primary retention member having an expanded state and disposed on said elongated member and axially and radially surrounding the back-up retention member, the primary retention member also having an inflation port, the inflation port not in fluid communication with the drainage lumen, the primary retention member also adapted in the expanded state to abut a bladder wall to seal a urethra;
    whereby said back-up retention member can maintain the position of the catheter in a patient should said primary retention member fail in the expanded state.

2. The catheter of claim 1, wherein said back-up retention member comprises a first balloon (20) having a collapsed state and wherein said elongated member has a first inflation lumen (21) extending longitudinally therein and communicating internally with said first balloon.

3. The catheter of claim 2, wherein said primary retention member comprises a second balloon (22) disposed around said first balloon and having a collapsed state and wherein said elongated member has a second inflation lumen (23) extending longitudinally therein and communicating internally with said second balloon and externally with said first balloon.

4. The catheter of claim 3 further comprising a first valve (27) disposed at least near a proximal end (28) of said first inflation lumen.

5. The catheter of claim 4 further comprising a second valve (29) disposed at least near a proximal end (30) of said second inflation lumen.

6. The catheter of claim 1, wherein said primary retention member comprises a balloon disposed around said primary retention member and having a collapsed state and wherein said elongated member has an inflation lumen extending longitudinally therein and communicating internally with said balloon.

7. The catheter of claim 1, wherein said distal end of said elongated member has an atraumatic shape (25).

8. The catheter of claim 1, wherein said elongated member includes a soft and flexible material.

9. The catheter of claim 8, wherein said soft and flexible material comprises at least one from a group consisting of silicone, latex, and elastomeric materials.

10. The catheter of claim 8, wherein said retention members each includes said soft and flexible material.

11. The catheter of claim 1, wherein said elongated member includes a tether lumen (26) extending transversely therethrough and disposed at least near said distal end and distal said at least one external drainage port.

12. The catheter of claim 11 further comprising a tether (31) positionable through said tether lumen of said elongated member.

13. A back-up retention member drainage catheter (10) comprising:
    an elongated member of a soft and flexible material having a distal end, a proximal end, and a drainage lumen extending longitudinally therein and having at least one external drainage port disposed at least near said distal end; wherein said distal end of said elongated member includes a plug insertable into said drainage lumen and at least one inflation lumen, said plug having an atraumatic shape and closing said drainage lumen and at least one inflation lumen thereat;
    a first balloon of said soft and flexible material having an expanded and a collapsed state and disposed on said elongated member at least near said distal end and proximal said at least one external drainage port, said elongated member having a first inflation lumen extending longitudinally therein and communicating internally with said first balloon; and
    a second balloon of said soft and flexible material having an expanded and a collapsed state and disposed on said elongated member and disposed over said first balloon, said elongated member having a second inflation lumen extending longitudinally therein and communicating internally with said second balloon and externally with said first balloon, the second balloon also adapted in the expanded state to abut a bladder wall to seal a urethra;
    whereby said first balloon can maintain the position of the catheter in a patient should said second balloon fail in the expanded state.

14. The catheter of claim 13, wherein said soft and flexible material comprises at least one of a group consisting of silicone, latex, and elastomeric materials.

15. The catheter of claim 14, wherein said distal end of said elongated member includes a plug (24) having an atraumatic shape (25) and closing said drainage lumen and said inflation lumens thereat.

16. The catheter of claim 13, wherein said at least one external drainage port includes an external drainage port disposed at said distal end of said elongated member.

17. A back-up retention member drainage catheter comprising:
    an elongated member of silicone having a distal end, a proximal end, a drainage lumen extending longitudinally therein and having at least one external drainage port disposed at least near said distal end, and a tether lumen extending transversely therethrough and disposed at least near said distal end and distal said at least one external drainage port;

a first balloon of silicone having an expanded and a collapsed state and disposed on said elongated member at least near said distal end and proximal said at least one external drainage port, said elongated member having a first inflation lumen extending longitudinally therein and communicating internally with said first balloon;

a second balloon of silicone having an expanded and a collapsed state and disposed on said elongated member and axially and radially surrounding the first balloon, said elongated member having a second inflation lumen extending longitudinally therein and communicating internally with said second balloon and externally with said first balloon, said distal end of said elongated member including a plug insertable into said drainage lumen and at least one inflation lumen, said plug having an atraumatic shape and closing said drainage lumen and said inflation lumens thereat, the second balloon also adapted in the expanded state to abut a bladder wall to seal a urethra;

a first valve disposed at least near a proximal end of said first inflation lumen; and a second valve disposed at least near a proximal end of said second inflation lumen, whereby said first balloon can maintain the position of the catheter in a patient should said second balloon fail in the expanded state.

* * * * *